(12) United States Patent
Liu et al.

(10) Patent No.: US 10,695,190 B2
(45) Date of Patent: Jun. 30, 2020

(54) BONE EXPANDABLE DEVICE

(71) Applicant: I-Shou University, Kaohsiung (TW)

(72) Inventors: Pao-Hsin Liu, Kaohsiung (TW);
Shih-Hsuan Shen, Kaohsiung (TW)

(73) Assignee: I-SHOU UNIVERSITY, Kaohsiung (TW)

( * ) Notice: Subject to any disclaimer, the term of this patent is extended or adjusted under 35 U.S.C. 154(b) by 151 days.

(21) Appl. No.: 15/954,022

(22) Filed: Apr. 16, 2018

(65) Prior Publication Data
US 2018/0311047 A1 Nov. 1, 2018

(30) Foreign Application Priority Data
Apr. 26, 2017 (TW) .............................. 106113985 A

(51) Int. Cl.
*A61F 2/44* (2006.01)
*A61F 2/46* (2006.01)
*A61F 2/30* (2006.01)

(52) U.S. Cl.
CPC .......... *A61F 2/4425* (2013.01); *A61F 2/4601* (2013.01); *A61F 2002/30148* (2013.01); *A61F 2002/30471* (2013.01); *A61F 2002/443* (2013.01)

(58) Field of Classification Search
CPC ...... A61F 2/4425; A61F 2/443; A61F 2/4601; A61F 2002/30148; A61F 2002/30471; A61F 2002/443; A61B 17/8858
See application file for complete search history.

(56) References Cited

U.S. PATENT DOCUMENTS

| 6,176,882 B1 | 1/2001 | Biedermann et al. |
| 8,012,207 B2 | 9/2011 | Kim |
| 2007/0225807 A1 | 9/2007 | Phan et al. |
| 2011/0319997 A1 | 12/2011 | Glerum et al. |
| 2014/0257484 A1 | 9/2014 | Flower et al. |

FOREIGN PATENT DOCUMENTS

| CN | 104665961 A | 6/2015 |
| CN | 204683847 U | 10/2015 |
| WO | WO-2018200507 A1 * | 11/2018 ........... A61F 2/4455 |

* cited by examiner

*Primary Examiner* — Eric S Gibson
(74) *Attorney, Agent, or Firm* — Muncy, Geissler, Olds & Lowe, P.C.

(57) ABSTRACT

A bone expandable device comprises two expanding members, a retractable member and a fastener. The two expanding members are joined together for forming a cavity therebetween, each the expanding member includes two flexible parts and a fixed part. The two flexible parts are connected to the fixed part separately, and each the flexible part can be bent from the fixed part. The retractable member is disposed in the cavity and includes a first part and a second part. The first part is movably sleeved on the second part, and a length of the retractable member can be adjusted by moving the first part or the second part. The fastener is for fastening the two expanding members together. When the length of the retractable member is increasing, the two opposite ends of the retractable member would push against the four flexible parts to expand the flexible parts outwardly from the cavity.

10 Claims, 11 Drawing Sheets

BONE EXPANDABLE DEVICE

RELATED APPLICATIONS

The present application claims the priority of Taiwan Application No. 106113985, filed Apr. 26, 2017.

FIELD OF THE DISCLOSURE

The present invention relates to a bone expandable device, and more particularly to a bone expandable device for expanding the collapsed bones.

BACKGROUND

Osteoporosis usually causes bones collapse, such as the compressive fracture of spine, and the patients with this disease are becoming more and more in recent years. Though the surgeries and the medical instruments nowadays are improved considerably, there are still a lot of issues occurring when these surgeries and instruments are applied clinically, such as the excessive damage to vertebral bones, the secondary collapse of spine, the insufficient angle and height for rebuilding the collapsed vertebral bones, and the leakage of bone cement.

The current surgeries for treating the compressive fracture of spine include Vertebroplasty, Kyphoplasty and Vertebral expandable implant, and the vertebral expandable implant is newer clinical surgery. The vertebral bones are expanded along the direction of spine by using the metal expander and are injected with bone cement for fixing and recovering the collapsed spine.

Though all the above surgery methods can be applied for clinical treatment, there are some failure issues happened after using these surgery methods. For example, the Vertebroplasty method cannot recover the spine height and usually have the severe problems such as bone cement leakage. In Kyphoplasty surgery, there is a risk that the balloon may break during expansion, and the spine could collapse again due to losing the support after removing the balloon. In the surgery of vertebral expandable implant, the metal tools are used to expand the collapsed vertebral bones, however, it is difficult to control the expanding effects and the problems such as insufficient expanding height and insufficient space for injecting the bone cement usually happened, and the worse is that the inaccurate expanding height could result in the spinal curve deformation.

Therefore, a bone expandable device is provided by the present invention for overcoming the above issues.

SUMMARY

One objective of the present invention is to provide a bone expandable device for expanding the collapsed bones or vertebral body firmly and safely, thereby to maintain a space therebetween for injecting the bone cement. The bone expandable device can prevent the bone cement from leaking, can be applied to adjust the required height of rebuilding vertebral bones by the medical therapy unit according to the vertebral collapse degree, and can be applied to perform the angular adjustment for the deformed spine curve. Further, the bone expandable device has a shorter length in the closing state and can be adjusted with continuous or multi-stage heights to provide firmly supports for the vertebral bones.

The present invention provides a bone expandable device comprising two expanding members, a retractable member and a fastener.

The two expanding members are joining together for forming a cavity therebetween, and each the expanding member includes two flexible parts and a fixed part. A middle portion of each the expanding member is the fixed part, and two end portions of each the expanding member are the flexible parts. The two flexible parts are connected to and extending from the fixed part separately, and each the flexible part can be bent from a position adjacent to the fixed part. The fastener is for fastening the fixed parts of the two expanding members together.

The retractable member is disposed in the cavity and includes a first part and a second part. The first part is movably sleeved on the second part, and a length of the retractable member can be adjusted by moving the first part or the second part.

When the length of the retractable member is increasing, the two opposite ends of the retractable member would push against surfaces of four the flexible parts of the two expanding members facing the cavity, to expand the flexible parts outwardly from the cavity.

The retractable member has various modifications. In one embodiment, an inner surface of the first part and an outer surface of the second part are corresponding to each other and are formed with screw threads individually. The first part is sleeved and screwed onto the second part, and the length of the retractable member can be adjusted by rotating the first part or the second part.

When the first part and the second part are made to be screwed together as depicted above, at least one of the first part and the second part is formed with an operation hole, for inserting a tool from outside to rotate the first part or the second part.

In another embodiment of the retractable member, an inner surface of the first part and an outer surface of the second part are corresponding to each other and are formed with ratchet teeth individually, and the length of the retractable member can be adjusted by pulling the first part or the second part.

In a further embodiment of the retractable member, the first part includes at least one sliding chute and the second part includes at least one sliding block corresponding to the at least one sliding chute, and the length of the retractable member can be adjusted by pulling the first part or the second part.

The fastener also has various modifications. In one embodiment, the fastener is a C-type fastener for clamping the two fixed parts elastically.

In another embodiment, the fastener is a double buckle structure including two buckle parts, and at least one end of one the buckle part is hooked up with at least one end of the other buckle part correspondingly.

In a further embodiment, the fastener is a double buckle structure including two buckle parts, and at least one end of one the buckle part is bolted on at least one end of the other buckle part correspondingly.

Therefore, by applying the bone expandable device provided by the present invention, the retractable member can push against and spread the two expanding members for expanding the collapsed bones or vertebral body firmly and safely, thereby to maintain a space therebetween for injecting the bone cement. Besides, the bone expandable device, can prevent the bone cement from leaking effectively, can be applied to adjust the required height of rebuilding vertebral bones by the medical therapy unit according to the vertebral collapse degree, and can be applied to perform the angular adjustment for the deformed spine curve. Further, the bone expandable device has a shorter length in the closing state and can be adjusted with continuous or multistage heights to provide firmly supports for the vertebral bones.

The present invention will be further described in detail with reference to accompanying drawings and preferred embodiments as follows.

BRIEF DESCRIPTION OF THE DRAWINGS

Accompanying drawings are for providing further understanding of embodiments of the disclosure. The drawings form a part of the disclosure and are for illustrating the principle of the embodiments of the disclosure along with the literal description. Apparently, the drawings in the description below are merely some embodiments of the disclosure, a person skilled in the art can obtain other drawings according to these drawings without creative efforts. In the figures.

DETAILED DESCRIPTION OF PREFERRED EMBODIMENTS

The specific structural and functional details disclosed herein are only representative and are intended for describing exemplary embodiments of the disclosure. However, the disclosure can be embodied in many forms of substitution and should not be interpreted as merely limited to the embodiments described herein.

Figure 1A:
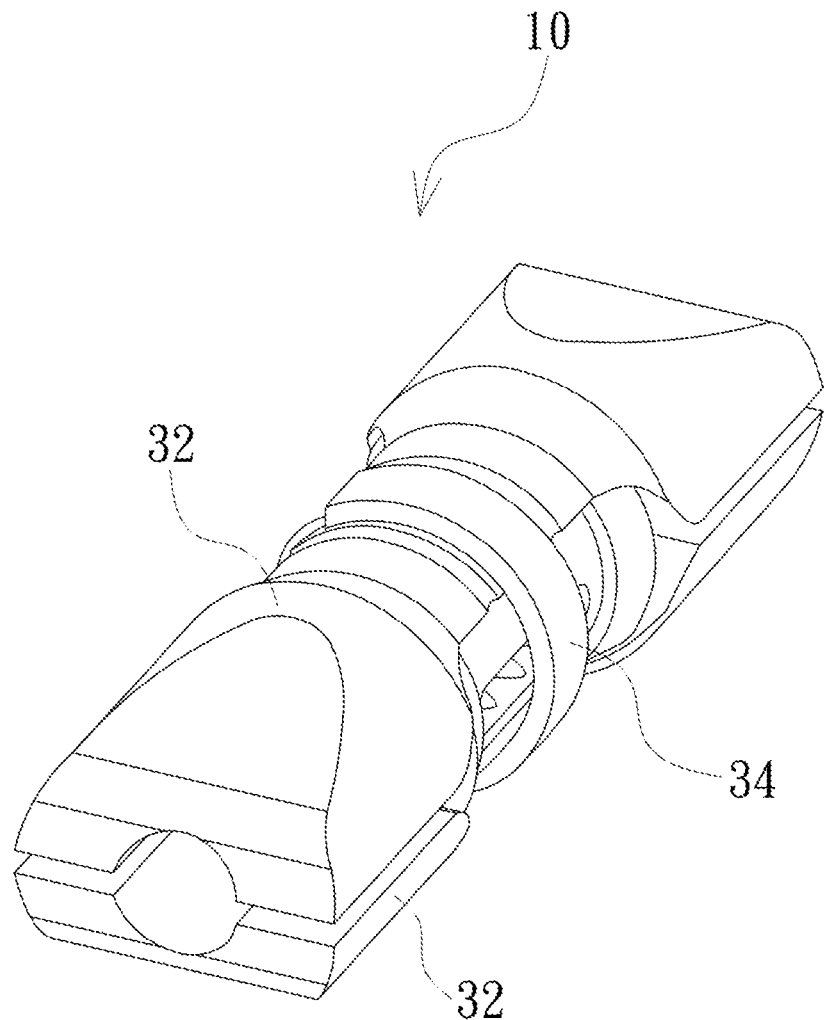
FIG. 1A is a schematic view of the bone expandable device in the closing state provided by the present invention.

Please refer to FIG. 1A, the schematic view of the bone expandable device 10 in the closing state provided by the present invention is shown. The fastener 34 is for fastening the two expanding members 32 stacked up and down, to join the two expanding members 32 together as a capsule for forming a cavity therebetween. The closing state of bone expandable device 10 has a small volume, beneficial for implanting into collapsed bones, for instance, implanting into collapsed vertebral bones.

Figure 1B:
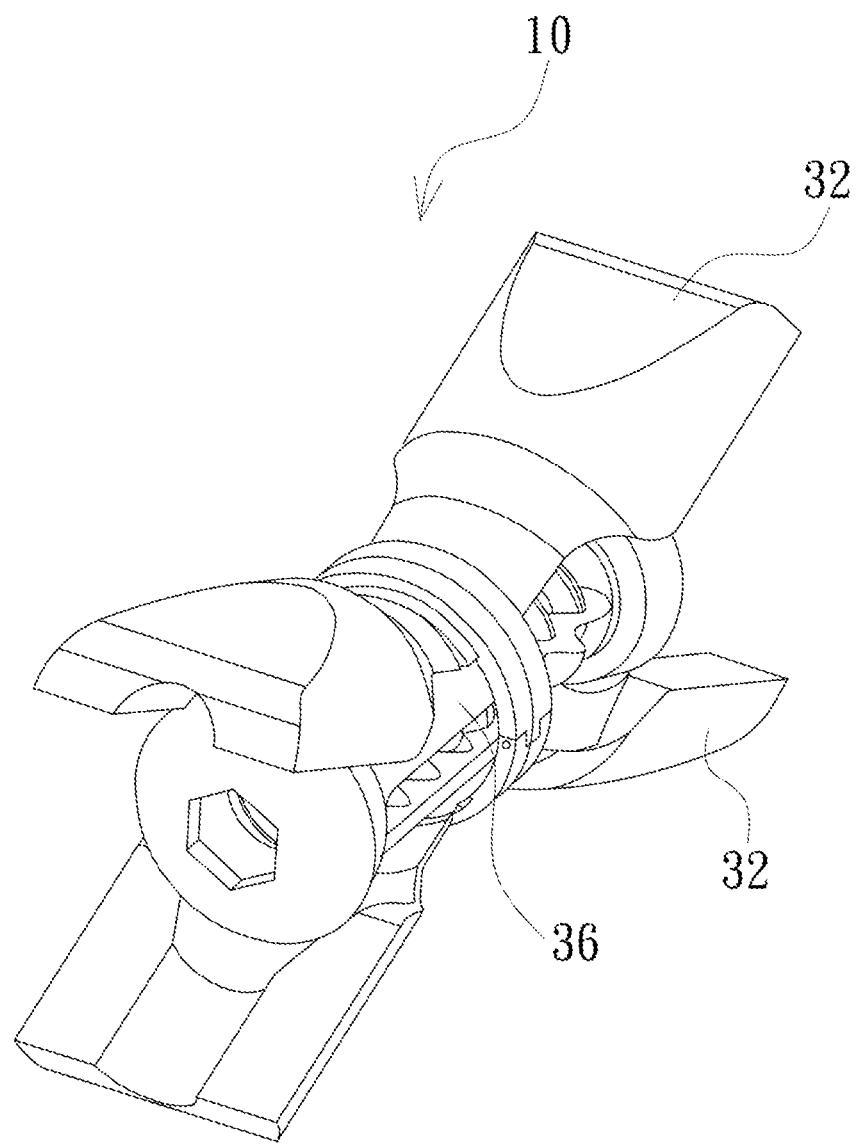
FIG. 1B is a schematic view of the bone expandable device in the expanding state provided by the present invention.

Please refer to FIG. 1B, the schematic view of the bone expandable device 10 in the expanding state provided by the present invention is shown. The bolt set 36 is stretching to expand the two ends of each the expanding member 32, for extending and supporting the collapsed bones, for instance, extending the collapsed vertebral bones.

Figure 2A:
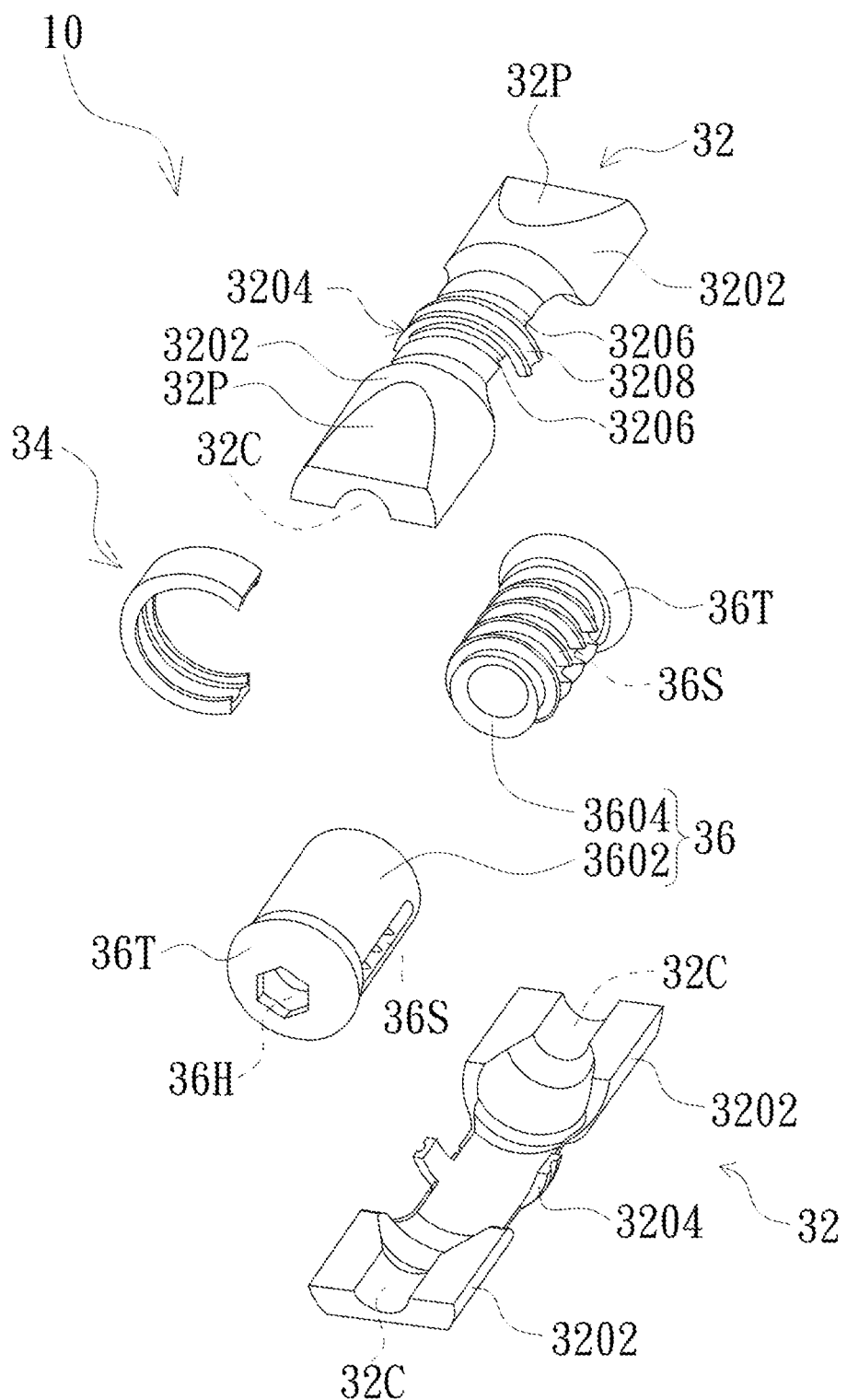
FIG. 2A is an explosion view of the bone expandable device provided by the present invention.
Figure 2B:
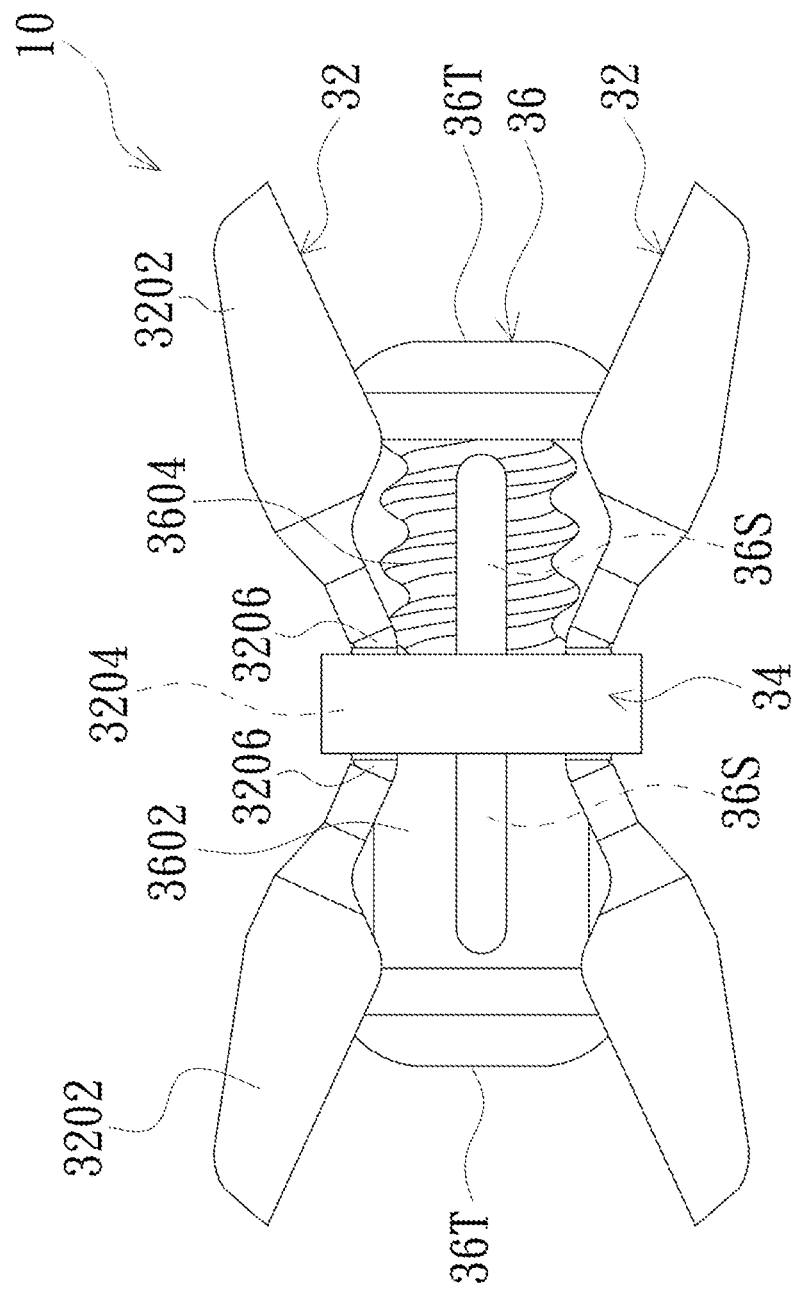
FIG. 2B is a side view of the bone expandable device in the expanding state provided by the present invention.

Please refer to FIG. 2A and FIG. 2B. FIG. 2A is an explosion view of the bone expandable device 10 provided by the present invention. FIG. 2B is a side view of the bone expandable device 10 in the expanding state. The bone expandable device 10 provided by the present invention comprises two the expanding members 32, the retractable member such as the bolt set 36 and the fastener 34.

Each the expanding member 32 includes two flexible parts 3202 disposed at two ends and a fixed part 3204. The middle portion of each the expanding member 32 is the fixed part 3204, and the two end portions of each the expanding member 32 are the flexible parts 3202. The two flexible parts 3202 are connected with and extending from the fixed part 3204 separately, and the portion of the flexible part 3202 adjacent to the fixed part 3204 is serving as a deformation part 3206. The deformation part 3206 is thinner or has a weak structural strength, thereby easy to be bent. Therefore, by bending the deformation part 3206 at the position the flexible parts 3202 adjacent to the fixed part 3204, the flexible parts 3202 can be bent and extending outwardly relative to the fixed part 3204.

The surface structure on outside of the fixed part 3204 is serving as a fastening part 3208. The structure shape of the fastening part 3208 is fitting to the inner structure shape of the fastener 34, so the fastener 34 can be fastened stably on the fastening part 3208, thereby to have the two expanding members 32 stacked up and down for forming a capsule-like structure. In a preferred embodiment, the two expanding members 32 are made of thinner steel sheets.

In this embodiment, the retractable member is the bolt set 36, and the bolt set 36 is disposed in the cavity. The first part and the second part are the nut part 3602 and the screw part 3604 individually. Namely, the bolt set 36 includes the nut part 3602 and the screw part 3604. The inner surface of the nut part 3602 and the outer surface of the screw part 3604 are corresponding to each other and are formed with screw threads individually, therefore the nut part 3602 is sleeved and screwed onto the screw part 3604.

The length of the bolt set 36 can be adjusted by rotating the nut part 3602 or the screw part 3604, thereby to elongate or shorten two ends of the bolt set 36 relative to the fixed part 3204 which is served as a center.

In a preferred embodiment, the nut part 3602 or the screw part 3604 is formed with an operation hole 36H on outer end thereof, such as the hexagon hole shown in Figs, for inserting a tool from outside to rotate the nut part 3602 or the screw part 3604, thereby to elongate or shorten the bolt set 36. Besides, the thread surfaces of the nut part 3602 and the screw part 3604 include at least one through hole 36S separately, beneficial for injecting the bone cement into the cavity.

The fastener 34 is applied to clamp firmly the two fixed parts 3204 of the two expanding members 32. Various embodiments of the fastener 34 are illustrated as below. In this embodiment, the fastener 34 is a C-type fastener for clamping the two fixed parts 3204 elastically.

The shape of the cavity in a side view is preferably a diamond shape or likes. When the length of the bolt set 36 is increasing, the two opposite ends 36T of the bolt set 36 would push against the surfaces of four the flexible parts 3202 of the two expanding members 32 facing the cavity, along the diamond shaped bevel surfaces of the cavity separately, thereby to expand the four flexible parts 3202 outwardly from the cavity. A surface of the flexible part 3202 facing the cavity has a guiding chute 32C extending along an elongation direction of the bolt set 36, beneficial for guiding the two opposite ends 36T sliding along a fixed direction. Besides, another surface of the flexible parts 3202 back to the cavity has a flat portion 32P, beneficial for contacting and supporting the collapsed bones with a large contacting area, to prevent the bones from being damaged again by the excessive stress due to the small contacting area.

Figure 3A:
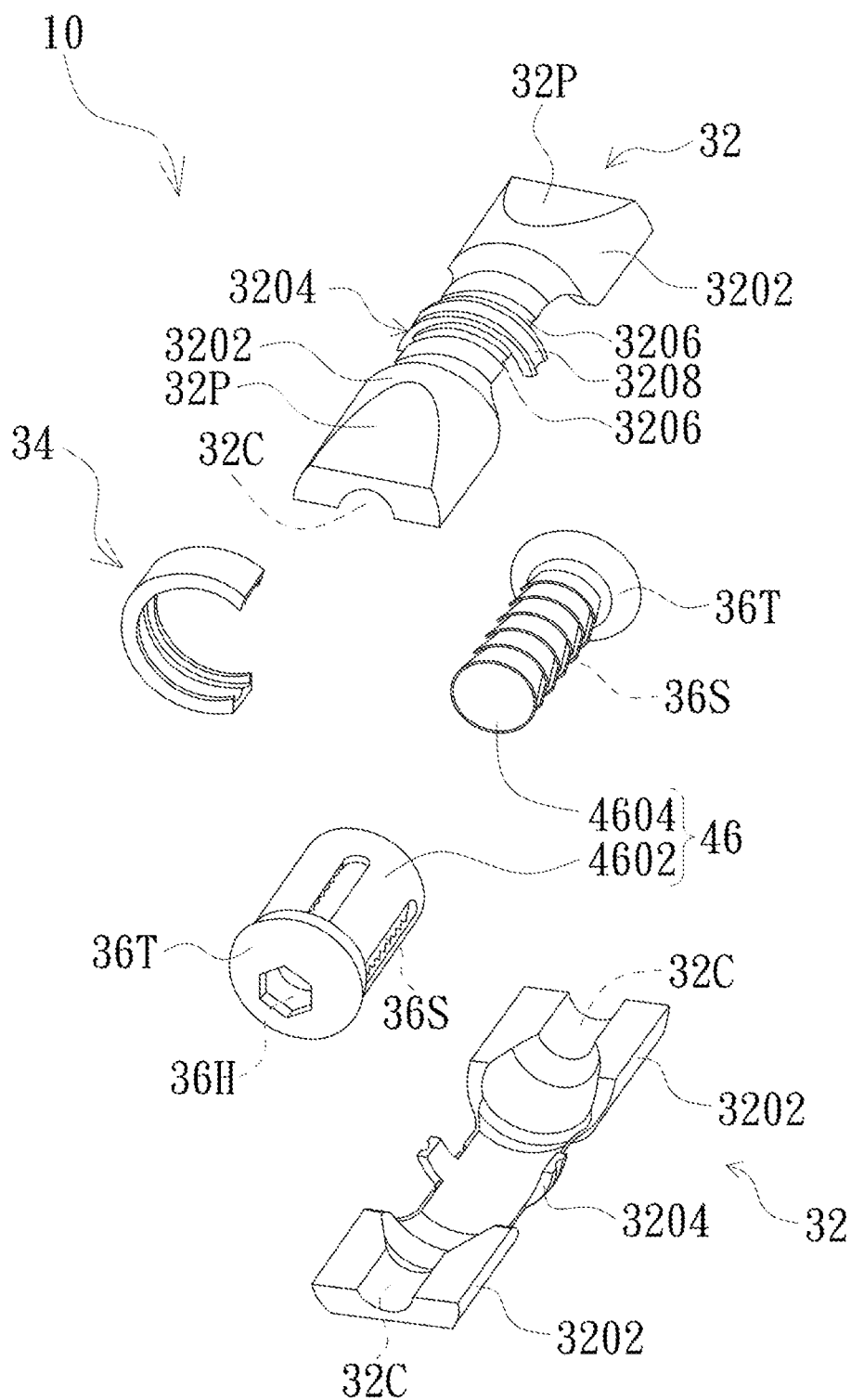
FIG. 3A and FIG. 3B are schematic views of the retractable member with ratchet teeth provided by the present invention.
Figure 3B:
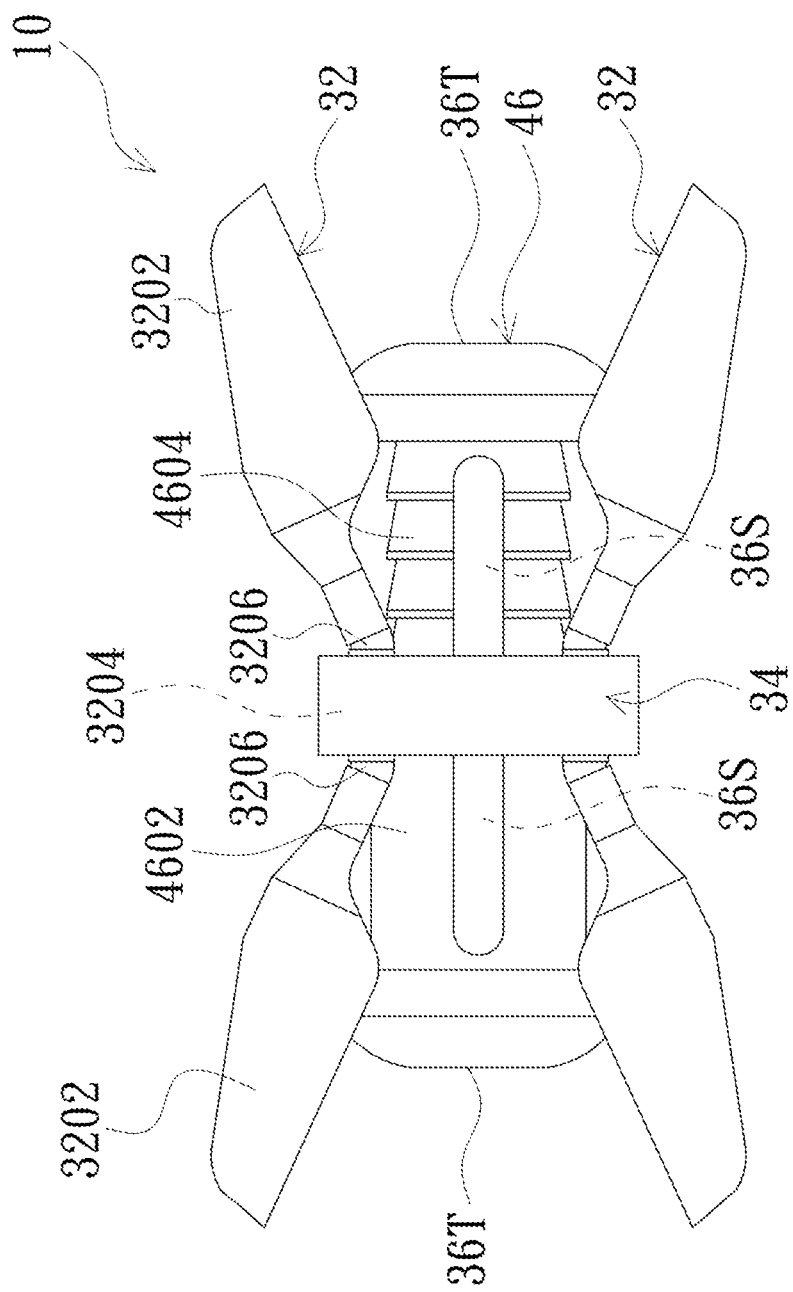

In the above embodiment, the retractable member is the bolt set 36, however, the retractable member may be made of other modifications. Please refer to FIG. 3A and FIG. 3B, the retractable member with ratchet teeth provided by the present invention is shown. In this embodiment, the retractable member is made of a ratchet set 46. The ratchet set 46 is also disposed in the cavity, the first part and the second part are the female ratchet part 4602 and the male ratchet part 4604 individually. Namely, the ratchet set 46 includes the female ratchet part 4602 and the male ratchet part 4604. The inner surface of the female ratchet part 4602 and the outer surface of the male ratchet part 4604 are corresponding to each other and are formed with circular ratchet teeth individually. The length of the ratchet set 46 can be elongated by pulling the female ratchet part 4602 or the male ratchet part 4604, and after the length adjustment the female ratchet part 4602 and the male ratchet part 4604 can stuck each other to fix the length of the ratchet set 46.

Figure 4A:
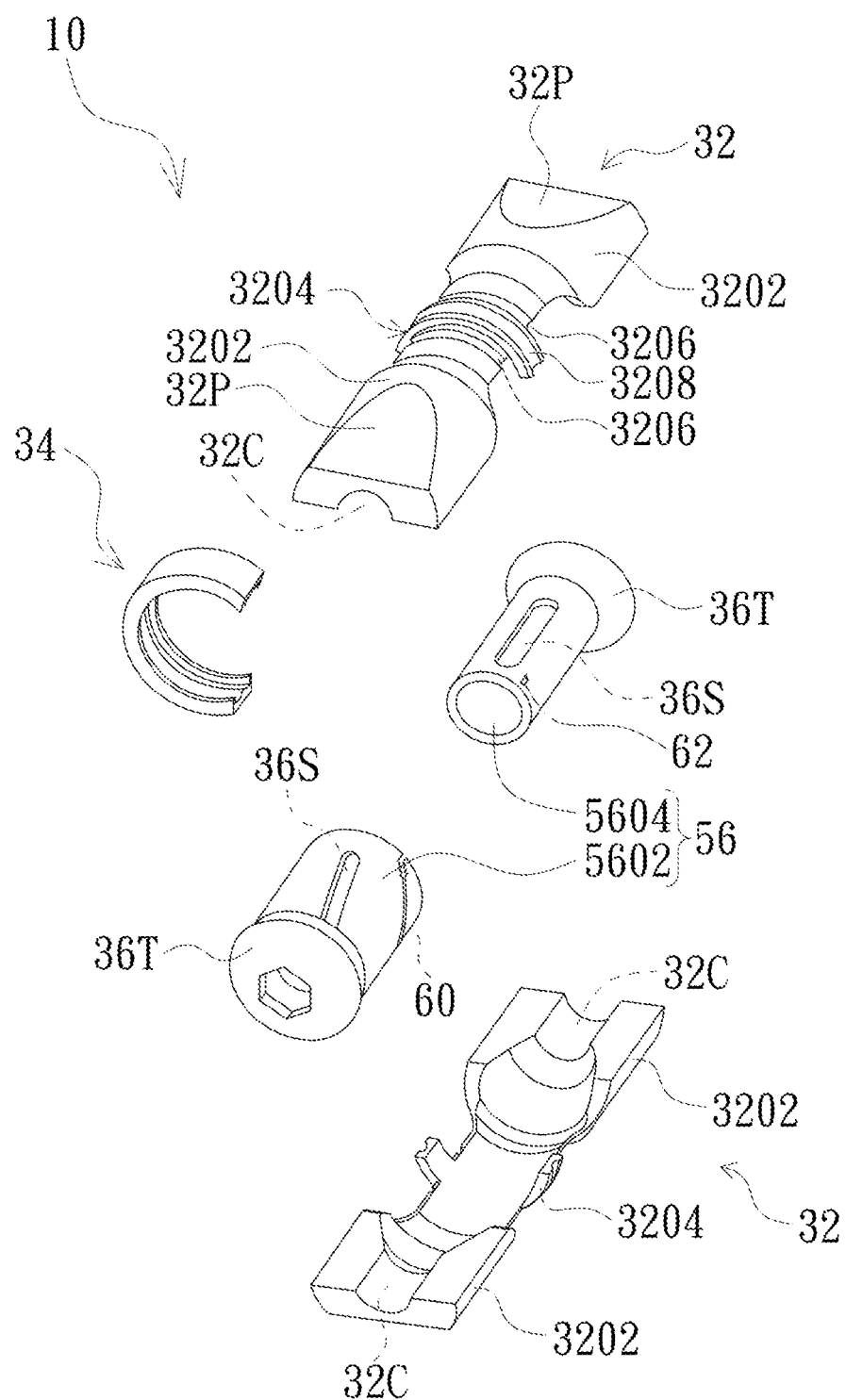
FIG. 4A and FIG. 4B are schematic views of the slide type of retractable member provided by the present invention.
Figure 4B:
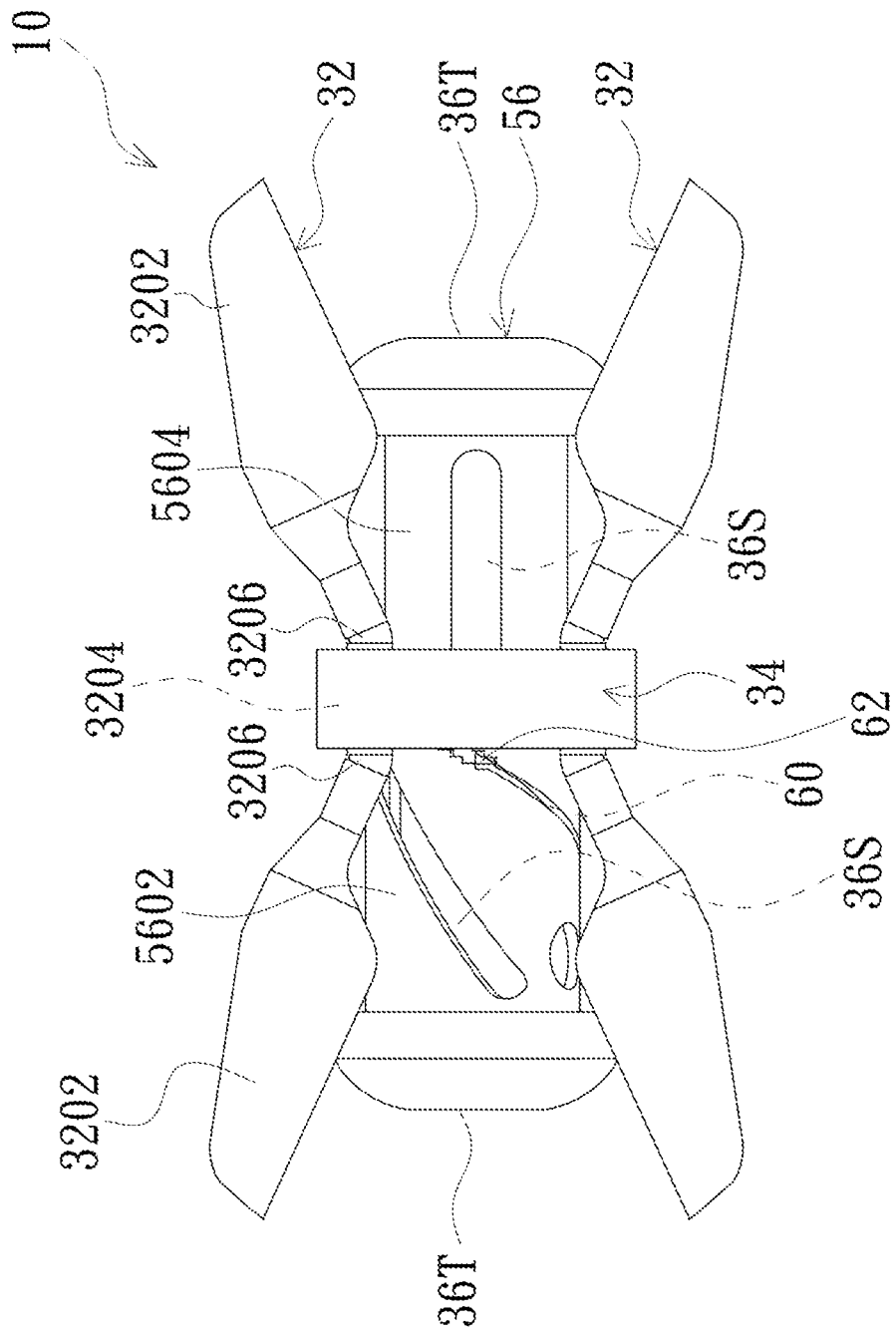

Please refer to FIG. 4A and FIG. 4B, the slide type of retractable member provided by the present invention is shown. In this embodiment, the retractable member is a slide set 56 disposed in the cavity, the first part and the second part are a female slide part 5602 and a male slide part 5604 individually. Namely, the slide set 56 includes the female slide part 5602 and the male slide part 5604. The female slide part 5602 includes at least one sliding chute 60, the male slide part 5604 includes at least one sliding block 62 corresponding to the sliding chute 60. As shown in this embodiment, the sliding chute 60 formed on the female slide part 5602 is long spiral-shaped, and the sliding block 62 is fixed on an outer surface of the male slide part 5604. A portion of the sliding chute 60 is made with zigzag slots for positioning the sliding block 62. By pulling the female slide part 5602 or the male slide part 5604, the sliding block 62 may slide in the sliding chute 60 for adjusting the length of the slide set 56 and stuck in the zigzag slot to fix the length of the slide set 56.

Figure 5:
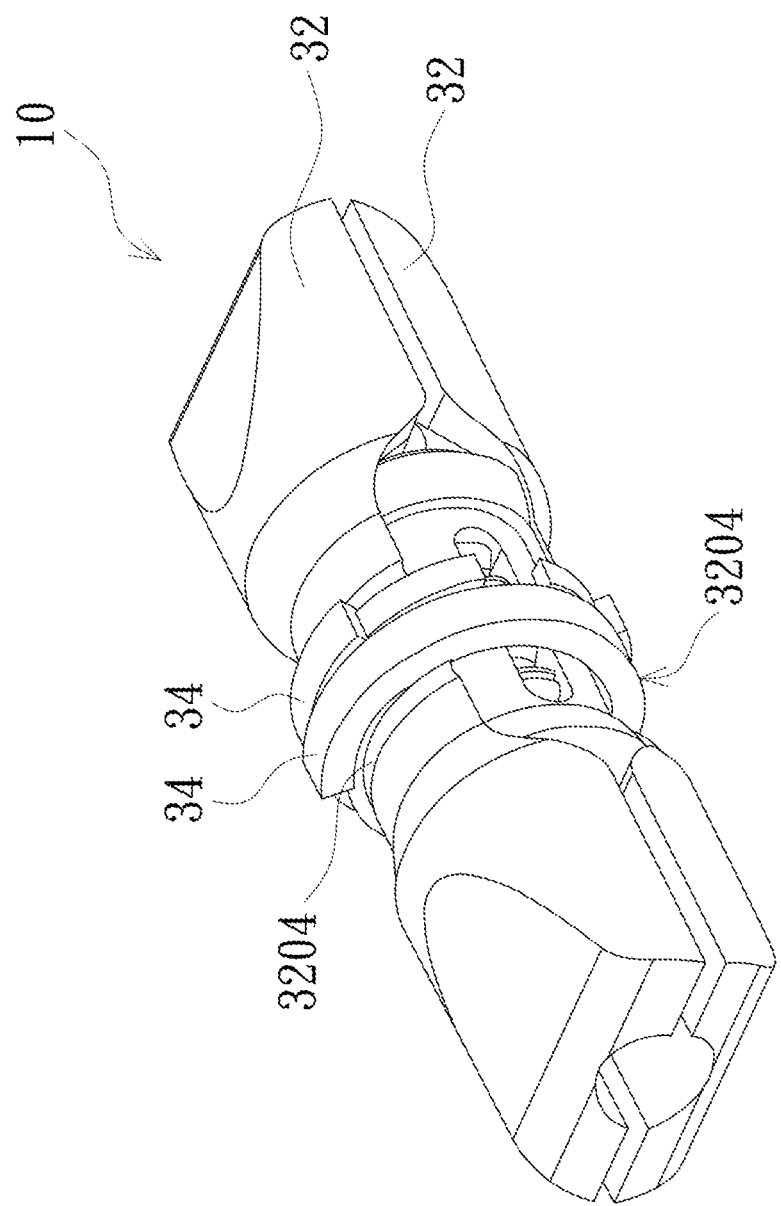
FIG. 5 is a schematic view illustrating another embodiment of the fastener provided by the present invention.

Please refer to FIG. 5, another embodiment of the fastener 34 provided by the present invention is shown. In this embodiment, the bone expandable device 10 includes two C-type fasteners 34 disposed opposite to each other for buckling. Namely, the two C-type fasteners 34 are arranged opposite to each other to clamp the fixed part 3204 of the two expanding members 32 individually. By buckling the two C-type fasteners 34 opposite to each other, the risk that the components of the bone expandable device 10 slipping off to each other or disassembling could be reduced.

Figure 6:
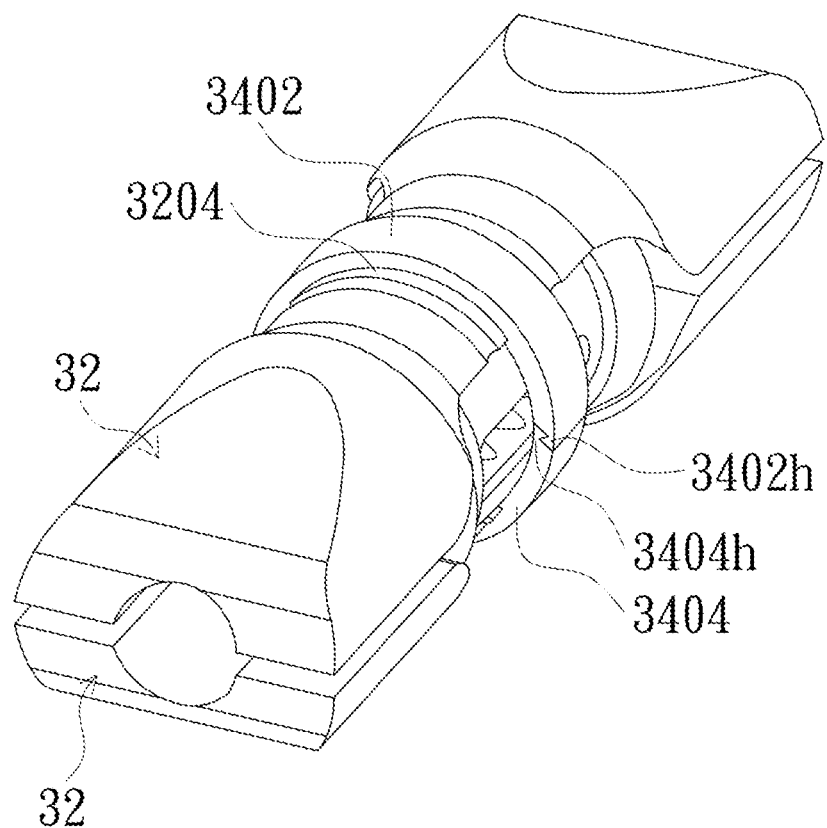
FIG. 6 is a schematic view illustrating further an embodiment of the fastener provided by the present invention.

Please refer to FIG. 6, another embodiment of the fastener 34 provided by the present invention is shown. The fastener 34 may be a double buckle structure including two buckle parts 3402 and 3404. In this embodiment, two the buckle parts 3402 and 3404 are disposed on the two fixed parts 3204 of the two expanding members 32 individually. Two ends of the buckle part 3402 are made with hook structures 3402h separately. Also, two ends of the buckle part 3404 are made with hook structures 3404h separately. Therefore, two the hook structures 3402h of the buckle part 3402 are corresponding to and may be hooked up with two the hook structures 3404h of the buckle part 3404 separately, thereby to fasten the two expanding members 32 together firmly by the buckle parts 3402 and 3404.

Figure 7:
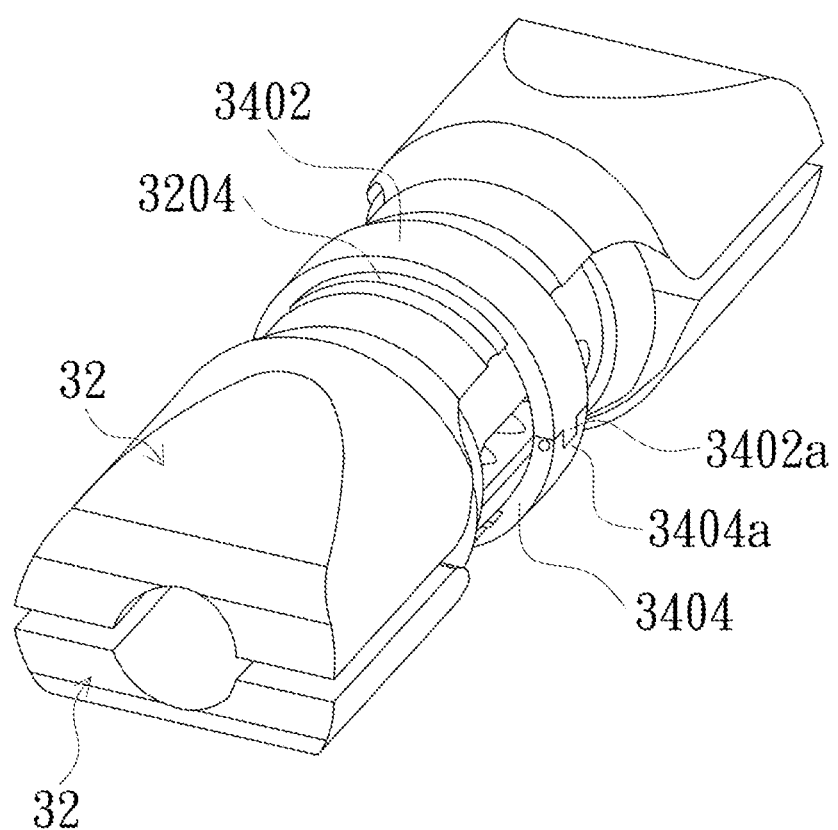
FIG. 7 is a schematic view illustrating another embodiment of the fastener provided by the present invention.

Please refer to FIG. 7, a further embodiment of the fastener 34 provided by the present invention is shown. The fastener 34 may be a double buckle structure including two buckle parts 3402 and 3404. In this embodiment, two the buckle parts 3402 and 3404 are disposed on the two fixed parts 3204 of the two expanding members 32 individually. Two ends of the buckle part 3402 are made with bolt structures 3402a separately. Also, two ends of the buckle part 3404 are made with bolt structures 3404a separately. The bolt structure 3402a is a convex structure with a first penetration hole, and the bolt structure 3404a is a concave structure with a second penetration hole. The bolt structure 3402a and the bolt structure 3404a are fitting to each other and may be fastened with a bolt inserting the first and second penetration holes. Therefore, two the bolt structures 3402a of the buckle part 3402 are correspond to and may be bolted on two the bolt structures 3404a of the buckle part 3404, thereby to fasten the two expanding members 32 together firmly by the buckle parts 3402 and 3404.

The bolt illustrated in FIG. 7 may be fixed or pluggable. Besides, the embodiments shown in FIG. 6 and FIG. 7 may be mixed up. Namely, a pair of the corresponding ends of the buckle parts 3402 and 3404 may be made with the hook structures 3402h and 3404h individually, and the other pair of the corresponding ends of the buckle parts 3402 and 3404 may be made with the bolt structures 3402a and 3404a individually, thereby to have more modifications.

Accordingly, when the bone expandable device 10 provided by the present invention is used, the retractable member can push against and spread the two expanding members for expanding the collapsed bones or vertebral body firmly and safely, thereby to maintain a space therebetween for injecting the bone cement. Besides, the bone expandable device, can prevent effectively the bone cement from leaking, can be applied to adjust the required height for rebuilding vertebral bones by the medical therapy unit according to the vertebral collapse degree, and can be applied to perform the angular adjustment for the deformed spine curve. Further, the bone expandable device has a shorter length in the closing state and can be adjusted with continuous or multistage heights to provide firmly supports for the vertebral bones.

The foregoing contents are detailed description of the disclosure in conjunction with specific preferred embodiments and concrete embodiments of the disclosure are not limited to these descriptions. For the person skilled in the art of the disclosure, without departing from the concept of the disclosure, simple deductions or substitutions can be made and should be included in the protection scope of the application.

What is claimed is:

1. A bone expandable device, comprising:
   two expanding members, joined together for forming a cavity therebetween, each of the expanding members including two flexible parts and a fixed part, wherein a middle portion of each of the expanding members is the fixed part and two end portions of each of the expanding members are the flexible parts, the two flexible parts are connected with and extending from the fixed part separately, and each of the flexible parts can be bent from a position adjacent to the fixed part, wherein a portion of each of the flexible parts at a position adjacent to the fixed part is thinner or has a weaker structural strength than other portions of the flexible parts for serving as a deformation part to be bent;
   a retractable member, disposed in the cavity, including a first part and a second part, wherein the second part couples to a sleeve of the first part, and a length of the retractable member can be adjusted by moving the first part or the second part; and a fastener, surrounding outsides of the two fixed parts of the two expanding members for clamping the two expanding members together;

wherein, when the length of the retractable member is increasing, two opposite ends of the retractable member would push against surfaces of the four flexible parts of the two expanding members facing the cavity, to expand the flexible parts outwardly from the cavity.

2. The bone expandable device according to claim 1, wherein an inner surface of the first part and an outer surface of the second part are corresponding to each other and are formed with screw threads individually, the second part is screwed into the sleeve of the first part, and the length of the retractable member can be adjusted by rotating the first part or the second part.

3. The bone expandable device according to claim 2, wherein at least one of the first part and the second part is formed with an operation hole on an outer end thereof, for inserting a tool from outside to rotate the first part or the second part.

4. The bone expandable device according to claim 1, wherein an inner surface of the first part and an outer surface of the second part are corresponding to each other and are formed with ratchet teeth individually, and the length of the retractable member can be adjusted by pulling the first part or the second part.

5. The bone expandable device according to claim 1, wherein the first part includes at least one sliding chute and the second part includes at least one sliding block corresponding to the at least one sliding chute, and the length of the retractable member can be adjusted by pulling the first part or the second part.

6. The bone expandable device according to claim 1, wherein a surface of the flexible part facing the cavity has a guiding chute extending along an elongation direction of the retractable member, and another surface of the flexible part has a flat portion opposite of the cavity.

7. The bone expandable device according to claim 1, wherein sidewalls of the first part and the second part both include at least one through hole separately.

8. The bone expandable device according to claim 1, wherein the fastener is a C-type fastener, for clamping the two fixed parts elastically.

9. The bone expandable device according to claim 1, wherein the fastener is a double buckle structure including two buckle parts, and at least one end of one the buckle part is hooked up with at least one end of the other buckle part correspondingly.

10. The bone expandable device according to claim 1, wherein the fastener is a double buckle structure including two buckle parts, and at least one end of one the buckle part is bolted on at least one end of the other buckle part correspondingly.

* * * * *